United States Patent [19]

Hall

[11] Patent Number: 5,158,967
[45] Date of Patent: Oct. 27, 1992

[54] 7-OXABICYCLOHEPTYL SUBSTITUTED HETEROCYCLIC AMIDE PROSTAGLANDIN ANALOGS USEFUL IN THE TREATMENT OF THROMBOTIC AND VASOSPASTIC DISEASE

[75] Inventor: Steven E. Hall, Pennington, N.J.

[73] Assignee: E. R. Squibb & Sons, Inc., Princeton, N.J.

[21] Appl. No.: 713,898

[22] Filed: Jun. 12, 1991

[51] Int. Cl.$^5$ .......................................... C07D 413/04
[52] U.S. Cl. ..................... 514/374; 514/79; 514/89; 514/92; 514/94; 514/183; 514/212; 514/399; 540/480; 540/602; 540/603; 546/196; 548/112; 548/236; 548/311.4; 549/463
[58] Field of Search ....................... 548/236; 514/374

[56] References Cited

U.S. PATENT DOCUMENTS

| | | | |
|---|---|---|---|
| 4,416,896 | 11/1983 | Nakane et al. | 549/463 |
| 4,418,076 | 11/1983 | Nakane et al. | 549/463 |
| 4,463,015 | 7/1984 | Haslanger et al. | 549/463 |
| 4,474,804 | 10/1984 | Das et al. | 549/463 |
| 4,522,949 | 6/1985 | Das et al. | 514/469 |
| 4,536,513 | 8/1985 | Das et al. | 514/469 |
| 4,556,675 | 12/1985 | Snitman et al. | 514/444 |
| 4,663,336 | 5/1987 | Nakane | 514/381 |
| 4,663,337 | 5/1987 | Das et al. | 514/382 |
| 5,100,889 | 3/1992 | Misra et al. | 514/374 |

FOREIGN PATENT DOCUMENTS 0374952 6/1990 European Pat. Off.
0391652 10/1990 European Pat. Off.

OTHER PUBLICATIONS

Derwent Abstr. As Belo Bioorg Chem, Apr. 3, 1981-SU278256 (Nov. 23, 1987).
Chem Abs. SA Selects: Prostaglandins Issue 12, 1988, 108:198903m. Kuz'mitskii, B. B. et al.
CA Selects: Prostaglandins, Issue 12, 1988, 108:204363d, Lakhvich, F. A. et al.

Primary Examiner—Donald G. Daus
Attorney, Agent, or Firm—Burton Rodney

[57] ABSTRACT

7-Oxabicycloheptyl substituted heterocyclic amide prostaglandin analogs are provided which are thromboxane $A_2$ ($TXA_2$) receptor antagonists or combined thromboxane $A_2$ receptor antagonist/thromboxane synthetase inhibitors and have the structural formula

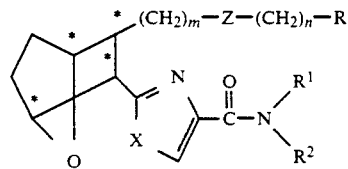

wherein R is $SO_3H$, $P(O)OR^3OH$ or $P(O)R^4OH$, X is O or NH, and Z, $R^1$, $R^2$, $R^3$ and $R^4$ are as defined herein.

14 Claims, No Drawings

7-OXABICYCLOHEPTYL SUBSTITUTED HETEROCYCLIC AMIDE PROSTAGLANDIN ANALOGS USEFUL IN THE TREATMENT OF THROMBOTIC AND VASOSPASTIC DISEASE

DESCRIPTION OF THE INVENTION

The present invention relates to 7-oxabicycloheptyl substituted heterocyclic amide prostaglandin analogs which are thromboxane $A_2$ (TXA$_2$) receptor antagonists or combined thromboxane $A_2$ receptor antagonist/thromboxane synthetase inhibitors useful, for example, in the treatment of thrombotic and/or vasospastic disease, and have good duration of action. These compounds have the structural formula I

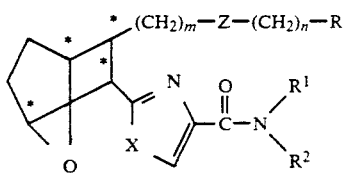

and including all stereoisomers thereof, wherein
m is 1, 2 or 3; n is 1, 2, 3 or 4;
Z is —(CH$_2$)$_2$—, —CH=CH— or

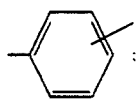

R is SO$_3$H, P(O)OR$^3$OH or P(O)R$^4$OH;
X is O or NH;
R$^1$ is hydrogen, lower alkyl, lower alkenyl, lower alkynyl, aralkyl, aryl, cycloalkyl, or cycloalkylalkyl;
R$^2$ is hydrogen, lower alkyl, aryl, or aralkyl; or
R$^1$ and R$^2$ together with the nitrogen to which they are linked may form a 5- to 8- membered ring;
R$^3$ is H or lower alkyl; and
R$^4$ is lower alkyl.

Thus, the compounds of the invention include the following types of compounds:

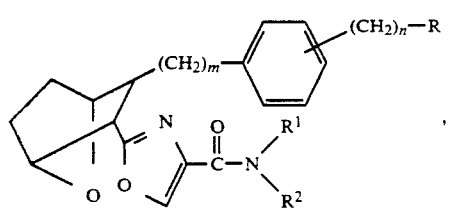

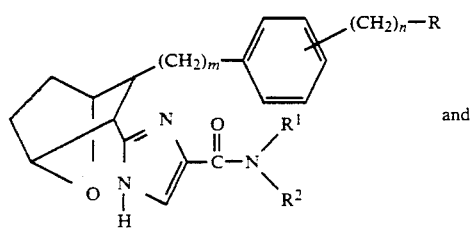

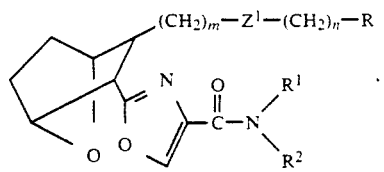

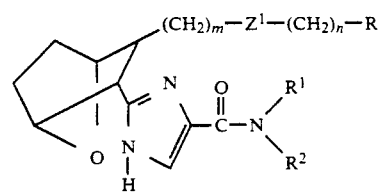

wherein formulae IC and ID, Z$^1$ is —CH=CH— or —(CH$_2$)$_2$—.

Preferred are compounds of formula Ix

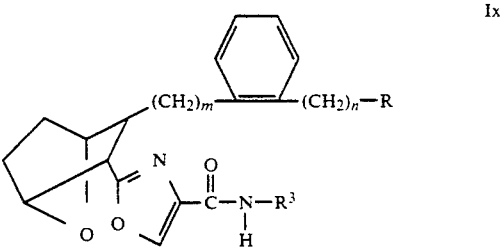

where R is SO$_3$H and R$^3$ is cycloalkylalkyl, m is 1 and n is 2 or 3.

The term "lower alkyl" or "alkyl" as employed herein includes both straight and branched chain radicals of up to 20 carbons, preferably 1 to 8 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like as well as such groups including 1, 2 or 3 halo substituents, an aryl substituent, an alkyl-aryl substituent, a haloaryl substituent, a cycloalkyl substituent, an alkylcycloalkyl substituent, hydroxy or a carboxy substituent.

The term "cycloalkyl" includes saturated cyclic hydrocarbon groups containing 3 to 12 carbons, preferably 3 to 8 carbons, which include cyclopropyl, cyclobutyl, cyclopentyl, cyclohexyl, cycloheptyl, cyclooctyl, cyclodecyl and cyclododecyl, any of which groups may be substituted with substituents such as halogen, lower alkyl, alkoxy and/or hydroxy groups.

The term "aryl" or "Ar" as employed herein refers to monocyclic or bicyclic aromatic groups containing from 6 to 10 carbons in the ring portion, such as phenyl or naphthyl. Aryl (or Ar), phenyl or naphthyl may include substituted aryl, substituted phenyl or substituted naphthyl, which may include 1 or 2 substituents on either the phenyl or naphthyl such as lower alkyl, trifluoromethyl, halogen (Cl, Br, I or F), lower alkoxy, arylalkoxy, hydroxy, alkylthio, alkylsulfinyl, alkylsulfonyl, arylthio, arylsulfinyl and/or arylsulfonyl.

The term "aralkyl", "aryl-alkyl" or "aryl-lower alkyl" as used herein refers to lower alkyl groups as discussed above having an aryl substituent, such as benzyl.

The term "lower alkoxy", "alkoxy" or "aralkoxy" includes any of the above lower alkyl, alkyl or aralkyl groups linked to an oxygen atom.

The term "halogen" or "halo" as used herein refers to chlorine, bromine, fluorine or iodine with chlorine being preferred.

The term "lower alkenyl" or "alkenyl" as employed herein with respect to the $R^1$ substituent includes a carbon chain of up to 16 carbons, preferably 3 to 10 carbons, containing one double bond which will be separated from "N" by at least one saturated carbon moiety such as —$(CH_2)_q$— where q can be 1 to 14, such as 2-propenyl, 2-butenyl, 3-butenyl, 2-pentenyl, 4-pentenyl and the like, and may include a halogen substituent such as I, Cl, or F.

The term "lower alkynyl" or "alkynyl" as employed herein with respect to the $R^1$ substituent includes a carbon chain of up to 16 carbons, preferably 3 to 10 carbons, containing one triple bond which will be separated from "N" by at least one saturated carbon moiety such as —$(CH_2)_{q'}$— where q' can be 1 to 14, such as 2-propynyl, 2-butynyl, 3-butynyl and the like.

The compounds of formula I of the invention may be prepared as follows.

The various compounds of the invention where R is $SO_3H$ may be prepared starting with ester V

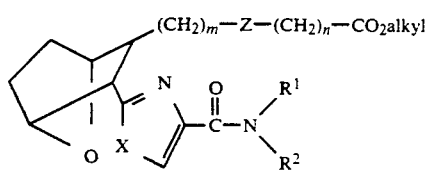

which is subjected to reduction by treating with a reducing agent such as lithium borohydride or sodium borohydride, in the presence of an inert organic solvent such as tetrahydrofuran, diethyl ether or dioxane to form the alcohol VI

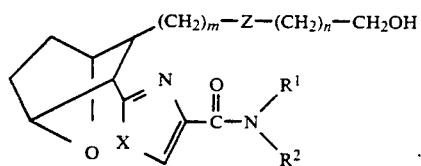

Alcohol VI is made to undergo an activation reaction wherein alcohol VI is treated with an activating agent such as methanesulfonylchloride in the presence of an organic base such as triethylamine, pyridine or diisopropylethylamine and an inert organic solvent such as methylene chloride, chloroform or tetrahydrofuran, to form the activated compound VII

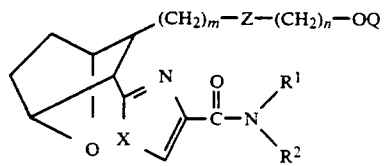

(wherein Q is an activating group).

The activated compound VII is then made to undergo a displacement reaction wherein VII is treated with potassium thioacetate or other alkali metal thioester such as sodium thioacetate, in the presence of an inert solvent such as dimethylsulfoxide or dimethylformamide, to form the thioester VIII

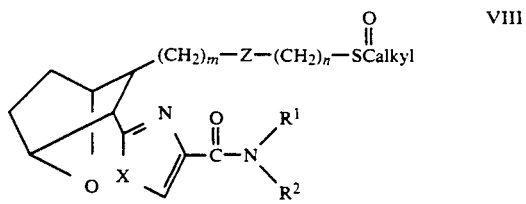

The thioester VIII is then oxidized, for example, by treatment with oxone in the presence of water and acetone, to form the compound of the invention IF

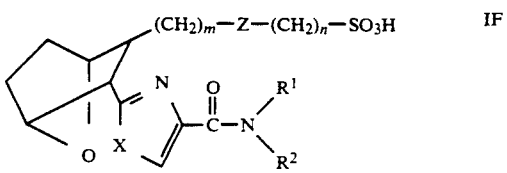

The compounds of formula I of the invention wherein R is —$P(O)OR^3OH$ may be prepared starting with alcohol VI which is made to undergo an activation reaction wherein alcohol VI is treated with an activator such as triphenyl phosphine dibromide in an inert solvent, such as chloroform, methylene chloride, or carbon tetrachloride to form the bromide IX

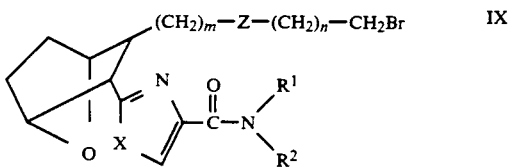

Bromide IX is then subjected to a displacement reaction wherein bromide IX is treated with a trialkyl phosphite such as trimethyl phosphite [$(CH_3O)_3P$] or triethyl phosphite [$(C_2H_5O)_3P$] using the trialkylphosphite as solvent at elevated temperatures of from about 100° C. to about 155° C. for about 2 to about 20 hours to form the phosphonate diester X

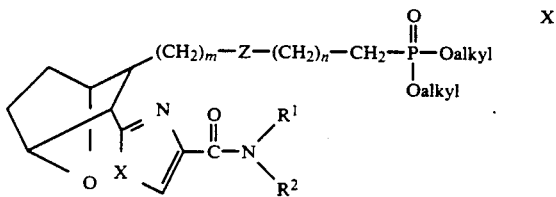

The phosphonate diester X is then hydrolyzed by treatment with an alkali metal hydroxide such as lithium hydroxide or sodium hydroxide to form the phosphonic acid compound of the invention having the structure IG

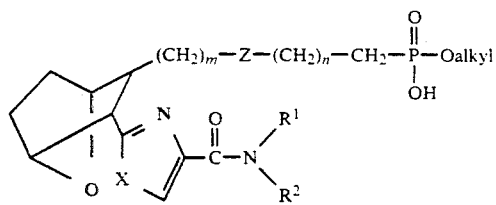

In an alternative procedure, compounds of the invention IF may be prepared by treatment of bromide IX with an alkali metal sulfite such as $Na_2SO_3$ in a suitable solvent such as water or tetrahydrofuran-water, at temperatures of from about 25° C. to about 100° C., followed by acidification with, for example, 1N HCl to form IF.

The compounds of formula I of the invention wherein R is —P(O)OR³OH and R³ is H may be prepared from phosphonate diester X by treatment with trimethylsilyl bromide, trimethylsilyl iodide, or trimethylsilyl chloride/sodium iodide in an inert solvent such as methylene chloride or acetonitrile at a temperature of about 0° C. to about 30° C. to form the phosphonic acid IH The compounds of formula I of the invention wherein R is —P(O)R⁴OH may be prepared using the procedure outlined for the conversion of bromide IX to acid IG except substituting R⁴—P(Oalkyl)₂ for P(Oalkyl)₃ to form phosphinic acid IJ.

The starting esters V may be prepared as disclosed in European Patent Application No. 0374952 and European Patent Application No. 0391652 which correspond to U.S. application Ser. No. 540,026 filed Jun. 18, 1990, now U.S. Pat. No. 5,100,889, which is incorporated herein by reference.

The compounds of this invention have four centers of asymmetry as indicated by the asterisks in formula I. However, it will be apparent that each of the formulae set out above which do not include asterisks still represent all of the possible stereoisomers thereof. All of the various stereoisomeric forms are within the scope of the invention.

The various stereoisomeric forms of the compounds of the invention, namely, cis-exo, cis-endo and all trans forms and stereoisomeric pairs may be prepared by employing starting materials and following the procedures as outlined in U.S. Pat. No. 4,143,054. Examples of such stereoisomers are set out below.

(cis-endo)

(cis-exo)

(trans)

(trans)

The nucleus in each of the compounds of the invention is depicted as for matter of convenience; it will also be appreciated that the nucleus in the compounds of the invention may be depicted as The compounds of this invention are thromboxane receptor antagonists and as such are useful as inhibitors of thromboxane receptor mediated actions. The term "thromboxane receptor antagonist" includes compounds which are so-called thromboxane A₂ receptor antagonists, thromboxane A₂ antagonists, thromboxane A₂/prostaglandin endoperoxide antagonists, TP-receptor antagonists, or thromboxane antagonists.

The compounds of the invention are also thromboxane synthetase inhibitors and thus are useful as inhibitors of thromboxane production.

The compounds of this invention are useful as inhibitors of platelet function, i.e., for the prevention and treatment of thrombotic vascular occlusive disorders, whether complete or partial, for example, arterial thrombosis, including that of the coronary, cerebral, ophthalmic, hepatic, mesenteric, renal, peripheral arteries or vascular or organ grafts, unstable angina, transient ischemic attacks, or intermittent claudication. They may be useful to prevent thrombosis following vascular injury produced in the course of diagnostic or therapeutic procedures such as endarterectomy or angiography. The compounds may be useful in the treatment or prevention of disorders characterized by platelet consumption and/or activation, including, platelet activation, dysfunction, and/or loss during extracorporeal circulation, the use of radiographic contrast agents, thrombotic thrombocytopenia purpura, disseminated intravascular coagulation, purpura fulminans, hemolytic transfusion reaction, or hemolytic uremic syndrome, systemic lupus, cyclosporine-induced renal toxicity, pulmonary hypertension, side effects from dialysis, or abdominal aortic aneurism repair. The compounds may be used in the treatment of venous thrombosis or embolism, including pulmonary embolism, deep venous thrombosis, hepatic vein thrombosis, and renal vein thrombosis.

The compounds of this invention are useful as inhibitors of arterial or venous vasoconstriction. Accordingly, they may be useful to prevent vasoconstriction associated with unstable angina, chronic stable angina, and variant, or Prinzmetal's angina, Raynaud's syndrome, migraine headache, vasospasm of the coronary, cerebral, ophthalmic, hepatic, mesenteric, renal, peripheral arteries or vascular grafts, vascular injury such as that associated with surgery or trauma. Hypertension of pregnancy, the hepato-renal syndrome, and pulmonary hypertension are additional examples of vasoconstrictive disorders treatable by the compounds of this invention.

The compounds of this invention are useful as inhibitors of bronchoconstriction, i.e., airway hyperresponsiveness, allergic bronchospasm, asthma, and bronchoconstrictive responses to environmental, infectious, noxious or mechanical stimuli.

The compounds of this invention are useful as inhibitors of ischemic and reperfusion injury to various tissues, including, myocardium, skin, brain, bowel, or kidney, alone or in combination with other agents intended to restore blood flow. For example, these compounds may be useful for improving postischemic myocardial function and decreasing myocardial infarct size. Ischemia caused by reduced blood flow during diagnostic or therapeutic procedures may benefit by treatment with these compounds, for example, they reduce the myocardial stunning observed after bypass surgery. In addition, they may be useful for reducing the tissue injury caused by a stroke.

The compounds of this invention may be useful in the prevention or treatment of other conditions including burns, diabetic retinopathy, tumor metastases and tardive dyskinesia. The compounds may be useful in potentiating diuretic-induced diuresis.

In addition, the thromboxane receptor antagonists of the invention may be used with a thrombolytic agent such as t-PA, streptokinase, urokinase, prourokinase or anisoylated plasminogenstreptokinase activator complex (APSAC) within 6 hours of a myocardial infarction. In such case, the thrombolytic agent may be used in amounts conventionally employed, for example, as disclosed in the Physicians' Desk Reference for reducing post-ischemic myocardial injury.

The compounds of the invention can be administered orally or parenterally to various mammalian species known to be subject to such maladies, e.g., humans, cats, dogs and the like in an effective amount within the dosage range of about 0.1 to about 100 mg/kg, preferably about 0.2 to about 50 mg/kg (or from about 1 to about 2500 mg, preferably from about 5 to about 2000 mg) on a regimen in single or 2 to 4 divided daily doses.

The active substance can be utilized in a composition such as tablet, capsule, solution or suspension containing about 5 to about 500 mg per unit of dosage of a compound or mixture of compounds of formula I or in topical form for wound healing (0.01 to 5% by weight compound of formula I, 1 to 5 treatments per day). They may be compounded in conventional matter with a physiologically acceptable vehicle or carrier, excipient, binder, preservative, stabilizer, flavor, etc., or with a topical carrier such as Plastibase (mineral oil gelled with polyethylene) as called for by accepted pharmaceutical practice. Also as indicated in the discussion above, certain members additionally serve as intermediates for other members of the group.

The compounds of the invention may also be administered topically to treat peripheral vascular diseases and as such may be formulated as a cream or ointment.

The following Examples represent preferred embodiments of the present invention. Unless otherwise indicated, all temperatures are expressed in degrees Centigrade.

EXAMPLE 1

[1S-(1α,2α,3α,4α)]-2-[[3-[4-[[(4-Cyclohexylbutyl)amino]carbonyl]-2-oxazolyl]-7-oxabicyclo[2.2.1]-hept-2-yl]methyl]benzeneethanesulfonic Acid

A.
[1S-(1α,2α,3α,4α)]-2-[[3-[4-[[(4-Cyclohexylbutyl)amino]carbonyl]-2-oxazolyl]-7-oxabicyclo[2.2.1]hept-2-yl]methyl]benzeneethanoic Acid, Methyl Ester The title ester was prepared as described in Example 81, Parts A to K of U.S. application Ser. No. 540,026, now U.S. Pat. No. 5,100,889 and European Patent Application 0391652.

B.
[1S-(1α,2α,3α,4α)]-2-[[3-[4-[[(4-Cyclohexylbutyl)amino]carbonyl]-2-oxazolyl]-7-oxabicyclo2.2.1]hept-2-yl]methyl]benzeneethanol To a stirred mixture of Part A ester (170 mg, 0.34 mmol) in 4 mL of dry THF under argon at room temperature was added LiBH$_4$ (247 mg, 11.2 mmol). The mixture was stirred at room temperature for 24 hours and acidified to pH 1 by the addition of 1N HCl solution. The mixture was diluted with 20 mL of water and extracted with dichloromethane (4×30 mL). The combined dichloromethane extracts were washed with 1N HCl solution (1×20 mL) and brine (1×40 mL). The organic layer was dried (MgSO$_4$), filtered and concentrated in vacuo. This was chromatographed on 24 g of Merck silica gel 60 using 2% CH$_3$OH/CH$_2$Cl$_2$ as eluant to give 73 mg (45%) of title alcohol.

TLC: silica gel, 2% CH$_3$OH/CH$_2$Cl$_2$, R$_f$ 0.22, I$_2$.

C.
[1S-(1α,2α,3α,4α)]-2-[[3-[4-[[(4-Cyclohexylbutyl)amino]carbonyl]-2-oxazolyl]-7-oxabicyclo[2.2.1]hept-2-yl]methyl]benzeneethanol, Methanesulfonate Ester To a stirred mixture of Part B alcohol (70 mg, 0.15 mmol), and triethylamine (Et$_3$N) (0.03 mL, 0.22 mmol) in 5 mL of dry dichloromethane was added methanesulfonyl chloride (MsCl) (15.0 μL, 0.19 mmol). The mixture was stirred at room temperature for 110 minutes and diluted with 40 mL of dichloromethane. The mixture was washed with 1N HCl solution (2×10 mL), saturated NaHCO$_3$ solution (1×10 mL) and brine (1×10 mL). The organic layer was dried (MgSO$_4$), filtered and concentrated in vacuo to give 81 mg of title mesylate in quantitative yield.

TLC: silica gel, 4% CH$_3$OH/CH$_2$Cl$_2$, R$_f$ 0.64, I$_2$.

D.
[1S-(1α,2α,3α,4α)]-2-[3-[4-[[(4-Cyclohexylbutyl)amino]carbonyl]-2-oxazolyl]-7-oxabicyclo[2.2.1]hept-2-yl]methyl]benzeneethanethiol, Acetate Ester To a stirred mixture of Part C mesylate (81.4 mg, 0.15 mmol) in 1.5 mL of dimethylsulfoxide (DMSO) was added potassium thioacetate (33.0 mg, 0.29 mmol). The mixture was stirred at room temperature for 5 hours and diluted with 100 mL of ether. The mixture was washed with saturated NaHCO$_3$ solution (2×15 mL). The organic layer was dried (MgSO$_4$), filtered and concentrated in vacuo. Purification was effected by flash chromatography on 10 g of Merck silica gel 60 using 1% CH$_3$OH/CH$_2$Cl$_2$ as eluant to give 62.7 mg (80%) of title thioacetate.

TLC: silica gel, 2% CH$_3$OH/CH$_2$Cl$_2$, R$_f$ 0.78, Ce(SO$_4$)$_2$.

E.
[1S-(1α,2α,3α,4α)]-2-[[3-[4-[[(4-Cyclohexylbutyl)amino]carbonyl]-2-oxazolyl]-7-oxabicyclo[2.2.1]hept-2-yl]methyl]benzeneethanesulfonic Acid To a stirred mixture of Part D thioacetate (60 mg, 0.12 mmol) in 4 mL of methanol and 2 mL of acetone was added an aqueous oxone solution (2 mL, preparation was described in Example 2). The mixture was stirred at room temperature for 63 hours and concentrated in vacuo. The residue was diluted with 5 mL of 1N HCl solution, saturated with NaCl and extracted with ethyl acetate (EtOAc) (4×20 mL). The combined EtOAc extracts were washed once with 15 mL of brine, dried (MgSO$_4$), filtered and concentrated in vacuo to give title sulfonic acid (55.6 mg, 92%).

TLC: silica gel, 1% acetic acid (HOAc) in 10% CH$_3$OH/CH$_2$Cl$_2$, R$_f$ 0.14, Ce(SO$_4$)$_2$.

EXAMPLE 2
[1S-(1α,2α,3α,4α)]-3-[[3-4-[[(4-Cyclohexylbutyl)amino]carbonyl]-2-oxazolyl]-7-oxabicyclo[2.2.1]-hept-2-yl]methyl]benzenepropanesulfonic Acid

A.
[1S-(1α,2α,3α,4α)]-2-[[3-[4-[(4-Cyclohexylbutyl)amino]carbonyl]-2-oxazolyl]-7-oxabicyclo[2.2.1]hept-2-yl]-methyl]benzenepropanol The title compound was prepared as described in Example 1, Parts A to N of U.S. application Ser. No. 540,026 and European Patent Application 391652.

B.
[1S-(1α,2α,3α,4α)]-2-[[3-[4-[[(4-Cyclohexylbutyl)amino]carbonyl]-2-oxazolyl]-7-oxabicyclo[2.2.1]hept-2-yl]methyl]benzenepropanol, Methanesulfonate Ester To a stirred mixture of Part A alcohol (88.2 mg, 0.18 mmol) and Et$_3$N (37.0 μL, 0.27 mmol) in 3 mL of dry dichloromethane was added methanesulfonyl chloride (MsCl) (18.0 μL, 0.23 mmol). The mixture was stirred at room temperature for 1 hour and diluted with 40 mL of dichloromethane. The mixture was washed with 1N HCl solution (2×10 mL) and saturated NaHCO$_3$ solution (1×10 mL). The organic layer was dried (MgSO$_4$), filtered and concentrated in vacuo to give 102 mg of title mesylate in quantitative yield.

TLC: silica gel, 2% CH$_3$OH/CH$_2$Cl$_2$, R$_f$ 0.46, I$_2$.

C.
[1S-(1α,2α,3α,4α)]-2-[3-[4-[[(4-Cyclohexylbutyl)amino]carbonyl]-2-oxazolyl]-7-oxabicyclo2.2.1]hept-2-yl]methyl]benzenepropanethiol, Acetate Ester To a stirred mixture of Part B mesylate (102 mg, 0.18 mmol) in 3 mL of dry DMSO under argon was added potassium thioacetate (40.7 mg, 0.36 mmol). The mixture was heated at 90° C. for 70 minutes and cooled to room temperature. The mixture was diluted with 150 mL of ether and washed with saturated NaHCO$_3$ solution (3×30 mL) and brine (1×30 mL). The ether layer was dried (MgSO$_4$), filtered and concentrated in vacuo. This was chromatographed on 10 g of Merck silica gel 60 using 1% CH$_3$OH/CH$_2$Cl$_2$ as eluant to give 87.1 mg (88%) of title thioacetate.

TLC: silica gel, 2% CH$_3$OH/CH$_2$Cl$_2$, R$_f$ 0.78, Ce(SO$_4$)$_2$.

D.
[1S-(1α,2α,3α,4α)]-2-[[3-[4-[[(4-Cyclohexylbutyl)amino]carbonyl]-2-oxazolyl]-7-oxabicyclo[2.2.1]hept-2-yl]methyl]benzenepropanesulfonic Acid To a stirred mixture of Part C thioacetate (40 mg, 0.07 mmol) in 4 mL of methanol and 2 mL of acetone was added an aqueous oxone solution (1.5 mL of a solution of 15 g of oxone dissolved in 50 mL of water). This mixture was then diluted with 50 mL of methanol. The resulting precipitate was filtered off and the filtrate was concentrated in vacuo to about 20 mL. The mixture was diluted with water to 50 mL and used as is. The mixture was stirred at room temperature for 76 hours and concentrated in vacuo. The residue was diluted with 4 mL of 1N HCl solution, saturated with NaCl and extracted with EtOAc (4×10 mL). The combined EtOAc extracts were washed once with 10 mL of brine, dried (MgSO$_4$), filtered and concentrated in vacuo to give title sulfonic acid (43 mg, 88%). TLC: silica gel, 1% HOAc in 10% CH$_3$OH/CH$_2$Cl$_2$, R$_f$ 0.14, Ce(SO$_4$)$_2$.

EXAMPLE 3
1S-(1α,2α,3α,4α)]-[2-2-3-[4-[[(4-Cyclohexylbutyl)amino]carbonyl]-2-oxazolyl]-7-oxabicyclo[2.2.1]hept-2-yl]methyl]phenyl]ethyl]phosphonic Acid, Methyl Ester A. [1S-(1α,2α,3α,4α)]-2-[2-[[3-4-[[(4-Cyclohexylbutyl)amino]carbonyl]-2-oxazolyl]-7-oxabicyclo[2.2.1]hept-2-yl]methyl]phenyl]ethyl Bromide To a stirred solution of 1 mmol of triphenylphosphine in 10 mL of toluene at 0° C. is added 1 mmol of bromide.

The resultant slurry is stirred for 15 minutes at which time a solution of 1 mmol of Example 1, Part B alcohol and 1 mmol pyridine in toluene is added. The reaction mixture is stirred for 2 hours at 0° C. and then is isolated by extractive work-up to give the crude bromide which is purified by silica gel chromatography using hexanes-/ethyl acetate as eluant to afford title bromide.

B.
[1S-(1α,2α,3α,4α)]-[2-[2-[[3-[4-[(4-Cyclohexylbutyl-)amino]carbonyl]-2-oxazolyl]-7-oxabicyclo[2.2.1]hept-2-yl]methyl]phenyl]ethyl]phosphonic Acid, Dimethyl Ester A mixture of 10 mmol of Part A bromide and 10 mmol of trimethyl phosphite are stirred and heated to 130° C. for 1 hour. The crude product is purified by silica gel chromatography using $CH_3OH/CH_2Cl_2$ mixtures to afford the title phosphonate.

C.
[1S-(1α,2α,3α,4α)]-[2-[2-[[3-[4-[[(4-Cyclohexylbutyl-)amino]carbonyl]-2-oxazolyl]-7-oxabicyclo2.2.1]hept-2-yl]methyl]phenyl]ethyl]phosphonic Acid, Methyl Ester To a solution of 1 mmol of Part B phosphonate in 10 mL of $CH_3OH$ is added 2.0 mL of 1N NaOH solution. This mixture is stirred at 23° C. for 6 hours and then is concentrated in vacuo. The residue is diluted with 5 mL of 1N HCl and 5 mL of water and extracted with ethyl acetate. The organic layers are dried ($MgSO_4$), filtered and concentrated in vacuo to afford title compound.

EXAMPLE 4
[1S-(1α,2α,3α,4α)]-[2-[2-[[3-[4-[[(4-Cyclohexylbutyl-)amino)]carbonyl]-2-oxazolyl]-7-oxabicyclo-2.2.1]hept-2-yl]methyl]phenyl]ethyl]phosphonic Acid To a stirred solution of 1 mmol of Example 3, Part B phosphonate and 2 mmol of chlorotrimethylsilane in 1.0 mL of acetonitrile is added 2.0 mmol of sodium iodide. The reaction mixture is stirred for 15 minutes and the resultant precipitate is removed by filtration. The filtrate is concentrated in vacuo and then is treated with water. The aqueous solution is concentrated in vacuo to afford the title compound.

EXAMPLE 4A
1S-(1α,2α,3α,4α)]-[2-[2-[[3-[4-[[(4-Cyclohexylbutyl-)amino]carbonyl]-2-oxazolyl]-7-oxabicyclo-2.2.1]hept-2-yl]methyl]phenyl]ethyl]methylphosphinic Acid

A.
[1S-(1α,2α,3α,4α)]-[2-[2-[[3-[4-[[(4-Cyclohexylbutyl-)amino]carbonyl]-2-oxazolyl]-7-oxabicyclo[2.2.1]hept-2-yl]methyl]phenyl]ethyl]methylphosphinic Acid, Methyl Ester A mixture of 10 mmol of Example 3, Part A bromide and 10 mmol of methyl dimethylphosphite is stirred at 130° C. for 1 hour. The crude product is purified by silica gel chromatography using hexane/ethyl acetate to afford the title compound.

B.
[1S-(1α,2α,3α,4α)]-[2-[2-[[3-[4-[[(4-Cyclohexylbutyl-)amino]carbonyl]-2-oxazolyl]-7-oxabicyclo[2.2.1]hept-2-yl]methyl]phenyl]ethyl]methylphosphinic Acid To a stirred solution of 1 mmol of Part A phosphinate in 10 mL of $CH_3OH$ is added 2 mL of 1N NaOH solution. The reaction mixture is stirred for 6 hours and then is concentrated in vacuo. The residue is diluted with 5 mL 1N HCl and 5 mL $H_2O$ and then is extracted with ethyl acetate. The organic extracts are dried ($MgSO_4$), filtered and concentrated in vacuo to afford the title compound.

Following the procedures of Examples 1 to 4a and U.S. application Ser. No. 540,026 filed Jun. 18, 1990, the following compounds within the scope of the present invention may be prepared.

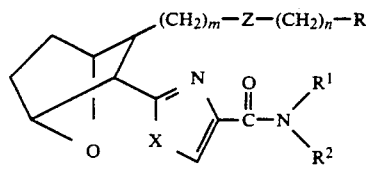

| Example No. | $(CH_2)_m$ m | $(CH_2)_n$ n | Z | X | $R^1$ | $R^2$ | R |
|---|---|---|---|---|---|---|---|
| 5 | 1 | 2 | CH=CH | O | $C_6H_{13}$ | $CH_3$ | $SO_3H$ |
| 6 | 2 | 2 | CH=CH | O | $-(CH_2)_2-\langle S \rangle$ (cyclohexyl with S) | $C_2H_5$ | $P(O)(CH_3)OH$ |
| 7 | 3 | 1 | $(CH_2)_2$ | NH | $\langle S \rangle$ (thiophene) | $i\text{-}C_3H_7$ | $P(O)(OCH_3)OH$ |
| 8 | 1 | 2 | $(CH_2)_2$ | O | $-(CH_2)_2-\langle C_6H_4 \rangle-Cl$ | H | $SO_3H$ |
| 9 | 1 | 2 | $(CH_2)_2$ | O | $i\text{-}C_3H_7$ | H | $P(O)(OCH_3)OH$ |

-continued

| Ex. No | m | n | | X | R² | R | R¹ |
|---|---|---|---|---|---|---|---|
| 10 | 1 | 3 | CH=CH | O | —CH₂-cyclohexyl | n-C₄H₉ | SO₃H |
| 11 | 1 | 2 | CH=CH | O | —(CH₂)₄-cyclohexyl | H | SO₃H |
| 12 | 1 | 2 | CH=CH | O | —(CH₂)₂-cyclohexyl | CH₃ | P(O)(C₃H₇)OH |
| 13 | 1 | 2 | (CH₂)₂ | O | cyclohexyl | H | SO₃H |
| 14 | 1 | 2 | CH=CH | NH | —(CH₂)₃-cyclopropyl | H | P(O)(OC₃H₇)OH |
| 15 | 2 | 2 | (CH₂)₂ | O | cyclobutyl | CH₂C₆H₅ | P(O)(OC₂H₅)OH |
| 16 | 1 | 2 | CH=CH | O | C₂H₅ | H | SO₃H |
| 17 | 1 | 3 | CH=CH | NH | 4-Cl-C₆H₄— | C₂H₅ | P(O)(OH)₂ |
| 18 | 1 | 2 | (CH₂)₂ | O | —(CH₂)₂C₆H₅ | CH₃ | SO₃H |
| 19 | 1 | 3 | CH=CH | O | n-C₃H₇ | CH₂C₆H₅ | P(O)(OC₂H₅)OH |
| 20 | 1 | 2 | CH=CH | NH | n-C₅H₁₁ | H | SO₃H |
| 21 | 2 | 3 | CH=CH | O | cyclohexyl | CH₃ | P(O)(OCH₃)OH |
| 22 | 1 | 2 | CH=CH | O | —(CH₂)₆— | | SO₃H |
| 23 | 1 | 2 | CH=CH | N | —(CH₂)₄-cyclohexyl | H | P(O)(OH)₂ |
| 24 | 2 | 2 | (CH₂)₂ | O | —(CH₂)₃-cyclohexyl | H | P(O)(C₂H₅)OH |
| 25 | 2 | 3 | CH=CH | O | C₆H₅ | C₆H₅ | P(O)(C₂H₅)OH |
| 26 | 1 | 2 | CH=CH | NH | —CH₂C₆H₅ | CH₂C₆H₅ | P(O)(OC₂H₅)OH |

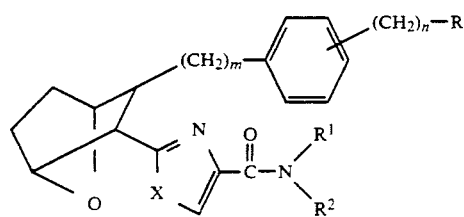

| Ex. No. | m | n | X | (position) | R² | R | R¹ |
|---|---|---|---|---|---|---|---|
| 27 | 1 | 2 | O | -(2) | H | SO₃H | CH₃ |
| 28 | 1 | 2 | O | -(2) | H | P(O)OCH₃OH | 4-OH-phenylbutyl |
| 29 | 1 | 2 | O | -(2) | H | SO₃H | propyl |

-continued

| | m | n | X | Z | R³ | R | R¹ |
|---|---|---|---|---|---|---|---|
| 30 | 1 | 2 | O | -(2) | H | P(O)(C₂H₅)OH | pentyl |
| 31 | 1 | 2 | O | -(2) | H | SO₃H | cyclohexylethyl |
| 32 | 1 | 2 | O | -(2) | H | P(O)(OCH₃)OH | t-butylbutyl |
| 33 | 1 | 2 | O | -(2) | H | SO₃H | 4-methoxyphenylbutyl |
| 34 | 1 | 2 | O | -(2) | H | P(O)(C₃H₇)OH | 4-cyclohexylbuten-2-yl |
| 35 | 1 | 2 | O | -(2) | H | SO₃H | 5-cyclohexylpenten-4-yl |
| 36 | 1 | 2 | O | -(2) | H | P(O)(OC₃H₇)OH | heptyl |
| 37 | 1 | 2 | O | -(2) | H | SO₃H | cyclohexyl |
| 38 | 1 | 2 | O | -(2) | H | P(O)(OC₂H₅)OH | isopropyl |
| 39 | 1 | 2 | O | -(2) | H | SO₃H | cyclohexyloctyl |
| 40 | 1 | 2 | N | -(2) | H | SO₃H | 4-phenylbutyl |
| 41 | 1 | 2 | N | -(2) | H | P(O)(OCH₃)OH | 4-phenylbutyl |
| 42 | 1 | 2 | O | -(2) | H | SO₃H | phenyl |
| 43 | 1 | 2 | O | -(2) | H | P(O)(OCH₃)OH | p-biphenyl |
| 44 | 1 | 2 | N | -(2) | H | SO₃H | 4-phenylbutyl |
| 45 | 1 | 2 | O | -(2) | H | P(O)(OH)₂ | 4-benzyloxyphenyl |
| 46 | 1 | 2 | O | -(2) | H | SO₃H | 4-hydroxyphenyl |
| 47 | 1 | 2 | O | -(2) | H | P(O)(OCH₃)OH | 3-iodo-propen-2-yl |
| 48 | 1 | 2 | O | -(2) | H | SO₃H | 4-(m-OH, o-iodophenyl)butyl |
| 49 | 1 | 2 | O | -(2) | H | SO₃H | 4-cyclohexylphenyl |
| 50 | 1 | 2 | O | -(2) | H | SO₃H | p-methoxyphenyl |
| 51 | 1 | 2 | O | -(2) | H | SO₃H | p-chlorophenyl |
| 52 | 1 | 2 | O | -(2) | H | P(O)(CH₃)OH | p-chlorophenyl |
| 53 | 1 | 2 | O | -(2) | H | P(O)(OC₂H₅)OH | p-chlorophenethyl |
| 54 | 1 | 2 | N | -(2) | H | SO₃H | t-butyl |
| 55 | 1 | 2 | O | -(2) | H | SO₃H | 1,1-dimethylpropyl |
| 56 | 1 | 2 | O | -(2) | H | SO₃H | n-C₁₈H₃₇ |
| 57 | 1 | 2 | O | -(2) | H | P(O)(OH)₂ | benzyl |
| 58 | 1 | 2 | O | -(2) | H | SO₃H | 5-hydroxy-5-methyl hexyl |
| 59 | 1 | 2 | O | -(2) | H | P(O)(OH)₂ | 5-carboxy-5-methyl hexyl |
| 60 | 1 | 2 | O | -(2) | H | SO₃H | H |
| 61 | 1 | 2 | O | -(2) | H | SO₃H | p-F-phenylbutyl |
| 62 | 1 | 2 | O | -(2) | H | SO₃H | C₁₀C₂₁ |
| 63 | 1 | 2 | O | -(2) | H | SO₃H | 2,2-dimethylbutyl |
| 64 | 1 | 2 | O | -(2) | H | P(O)(OCH₃)OH | 2,2-dimethypropyl |
| 65 | 1 | 2 | O | -(2) | H | SO₃H | 3,3-dimethylbutyl |
| 66 | 1 | 2 | O | -(2) | H | P(O)(OCH₃)OH | 2-(4-fluorophenyl)ethyl |
| 67 | 1 | 2 | O | -(2) | H | SO₃H | 2-phenylethyl |
| 68 | 1 | 2 | O | -(2) | H | SO₃H | cyclohexylbutyl |
| 69 | 1 | 2 | O | -(2) | H | P(O)(OCH₃)OH | cyclohexylbutyl |
| 70 | 1 | 2 | O | -(2) | H | SO₃H | cyclohexylpropyl |
| 71 | 1 | 2 | O | -(2) | H | SO₃H | cyclohexyl |
| 72 | 1 | 2 | O | -(2) | CH₃ | SO₃H | pentyl |
| 73 | 1 | 2 | O | -(2) | H | SO₃H | cyclohexylpentyl |
| 74 | 1 | 2 | O | -(2) | CH₃ | SO₃H | cyclohexylbutyl |
| 75 | 2 | 1 | O | -(2) | H | SO₃H | cyclohexylbutyl |
| 76 | 2 | 1 | O | -(3) | H | SO₃H | cyclohexylbutyl |
| 77 | 2 | 2 | O | -(2) | H | SO₃H | cyclohexylbutyl |
| 78 | 1 | 3 | O | -(2) | H | P(O)(OCH₃)OH | cyclohexylbutyl |
| 79 | 1 | 1 | O | -(2) | H | SO₃H | cyclohexylbutyl |
| 80 | 2 | 3 | O | -(3) | H | SO₃H | cyclohexylbutyl |
| 81 | 1 | 2 | N | -(2) | H | SO₃H | cyclohexylbutyl |
| 82 | 1 | 2 | O | -(2) | H | SO₃H | cyclohexylbutyl |
| 83 | 1 | 2 | O | -(2) | H | SO₃H | 6-heptynyl |

What is claimed is:

1. A compound having the formula

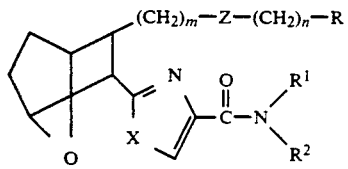

including all stereoisomers thereof, wherein
m is 1, 2 or 3;
n is 1, 2, 3 or 4;
Z is —(CH₂)₂—, —CH=CH— or

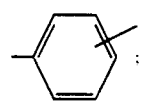

R is SO₃H;
X is O;
R¹ is hydrogen, alkyl, lower alkenyl containing 3 to 16 carbons, lower alkynyl having 3 to 16 carbons, phenyl, naphthyl, phenylalkyl, naphthylalkyl, cycloalkyl, or cycloalkylalkyl;
R² is hydrogen, lower alkyl, aryl, or aralkyl;
R³ is H or lower alkyl; and
R⁴ is lower alkyl;
the term "alkyl" or "lower alkyl" as employed herein alone or as part of another group refers to a radical having 1 to 20 carbons and the term "cycloalkyl" as employed herein alone or as part of another group refers to a radical having 3 to 12 carbons.

2. The compound as defined in claim 1 wherein m is 1 and n is 2 or 3.

3. The compound as defined in claim 1 wherein R¹ is cycloalkylalkyl.

4. The compound as defined in claim 1 wherein Z is

5. The compound as defined in claim 1 wherein Z is

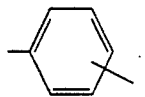

6. The compound as defined in claim 1 wherein X is O, $R^1$ is cycloalkylalkyl, m is 1, n is 2 or 3 and Z is

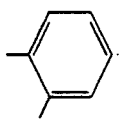

7. The compound as defined in claim 6 wherein R is $SO_3H$.

8. The compound as defined in claim 1 which is [1S-(1α,2α,3α,4α)]-2-[[3-[4-[[(4-cyclohexylbutyl)amino]butyl)amino]carbonyl]-2-oxazolyl]-7-oxabicyclo[2.2.1]hept-2-yl]methyl]benzenepropanoic sulfonic acid.

9. The compound as defined in claim 1 which is [1S-(1α,2α,3α,4α)]-3-[[3-[4-[[(4-cyclohexylbutyl)amino]carbonyl]-2-oxazolyl]-7-oxabicyclo[2.2.1]hept-2-yl]methyl]benzeneethanesulfonic acid.

10. A method of inhibiting platelet aggregation and bronchoconstriction, which comprises administering to the circulatory system of a mammalian host a therapeutically effective amount of a compound as defined in claim 1.

11. A composition for inhibiting platelet aggregation and bronchoconstriction comprising a therapeutically effective amount of a compound as defined in claim 1, and a pharmaceutically acceptable carrier therefor.

12. A method of inhibiting platelet aggregation which comprises administering to a mammalian host a therapeutically effective amount of a compound as defined in claim 1.

13. A method of inhibiting bronchoconstriction associated with asthma, which comprises administering to a mammalian host a therapeutically effective amount of a compound as defined in claim 1.

14. A method for improving post-ischemic myocardial function, which comprises administering to a mammalian host in need of such treatment a therapeutically effective amount of a compound as defined in claim 1.

* * * * *

UNITED STATES PATENT AND TRADEMARK OFFICE
CERTIFICATE OF CORRECTION

PATENT NO. : 5,158,967
DATED : October 27, 1992
INVENTOR(S) : Steven E. Hall

It is certified that error appears in the above-identified patent and that said Letters Patent is hereby corrected as shown below:

Column 16, line 51, the word "containing" should read --having--.

Column 18, line 1, delete the words "butyl)amino]".

Signed and Sealed this

Twelfth Day of October, 1993

Attest:

BRUCE LEHMAN

*Attesting Officer*  *Commissioner of Patents and Trademarks*